Aug 7, 1951 E. S. BOERNER Plant Pat. 1,024
ROSE PLANT
Filed May 29, 1950
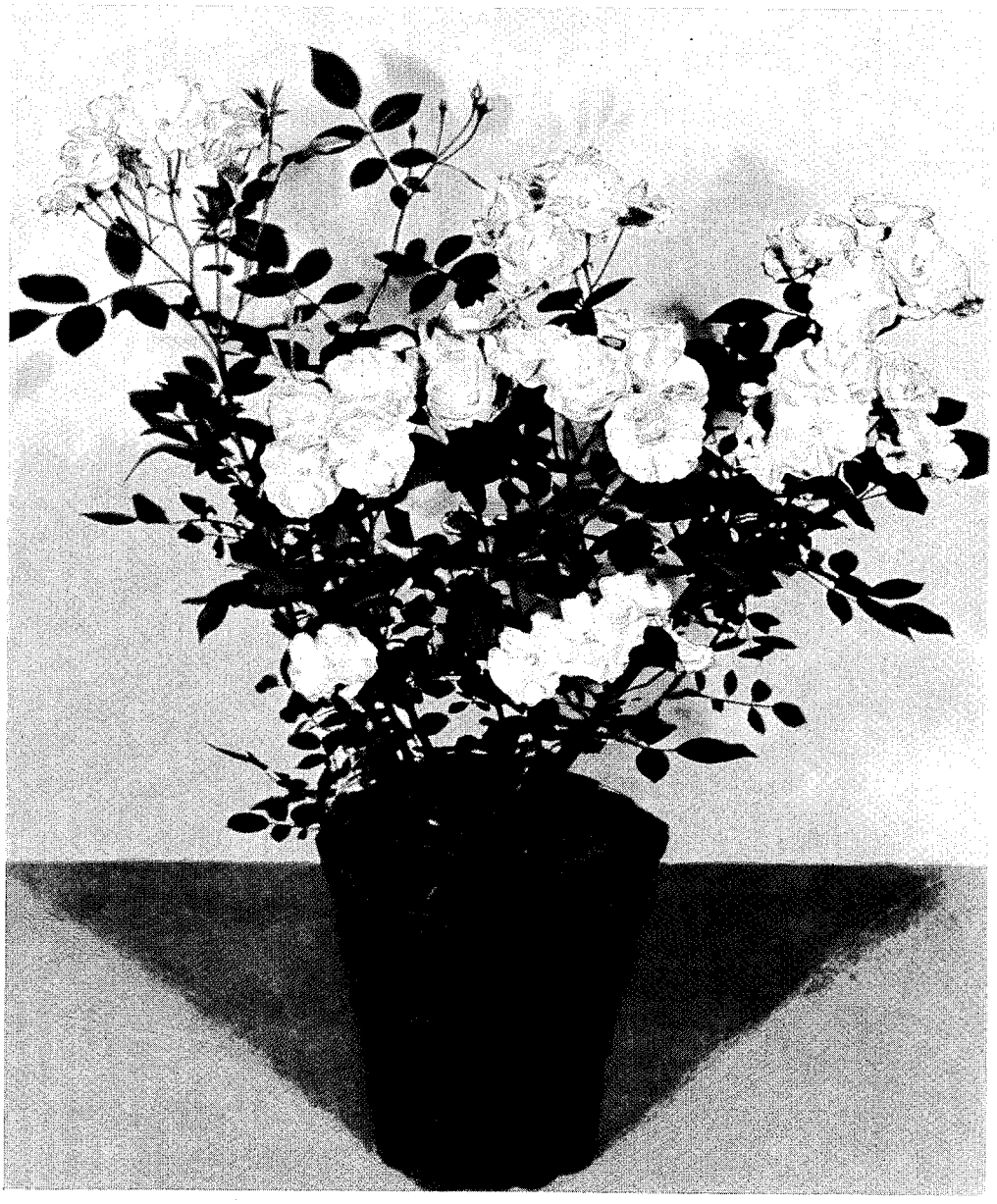
Inventor.
E. S. Boerner
By: Robbs & Cobb
Attorneys.

Patented Aug. 7, 1951 Plant Pat. 1,024

UNITED STATES PATENT OFFICE 1,024

ROSE PLANT

Eugene S. Boerner, Newark, N. Y., assignor to Jackson & Perkins Company, Newark, N. Y., a corporation of New York Application May 29, 1950, Serial No. 164,896

1 Claim. (Cl. 47—61)

The present invention relates to a new and distinct variety of rose plant of the polyantha class, originated by crossing the variety "Triumph d'Orleans" (unpatented) × "Mrs. Pierre S. Du Pont" (unpatented).

The primary objective in making this cross was to improve the color of the polyantha parent variety "Triumph d'Orleans." This objective was fully attained, as evidenced by the fact that the new variety has the same general polyantha habits as "Triumph d'Orleans," but has larger and brighter individual florets in the clusters, thereby making a better rose for florist pot plant use.

The improved color of the flowers of the new variety may be described as Spectrum Red, lightly overcast with Rose Doree, with the eye of the bloom White in color.

Other improved characteristics of this new variety are evidenced by its habit of having no thorns on the plant except for sharp hooks on the mid-rib of the under surface of each leaf, and by the freedom and ease of bloom when used as a pot plant.

Asexual reproduction of the new variety by budding at Newark, New York, and at Pleasanton, California, shows that the foregoing characteristics come true to form and are established and transmitted through succeeding propagations.

The accompanying drawing shows a specimen potted plant of the new variety, with the flowers and foliage in different stages of development.

The following is a detailed description of the new variety, with color terminology in accordance with Ridgeway's Color Standards and Nomenclature:

Parentage: Seedling.
*Seed parent.*—"Triumph d'Orleans."
*Pollen parent.*—"Mrs. Pierre S. Du Pont."
Classification:
*Botanic.*—Polyantha.
*Commercial.*—Floribunda.

*Flower*

(Observations made in the greenhouses at Newark, N. Y., late in the month of March, 1950.)

Blooming habit: Recurrent—continuous.
Bud:
*Size.*—Small.
*Form.*—Pointed. Is not affected by wet or hot weather.

*Color.*—When sepals first divide—Pomegranate Purple, Plate 12. When petals begin to unfurl—Carmine, Plate 1. When half blown—inside of petals: Spectrum Red, Plate 1; reverse of petals: Scarlet Red, Plate 1.

*Sepals.*—Slightly branched. Curl back when petals begin to unfurl. Color—Inside: Absinthe Green, Plate 31; Outside: Light Cress Green, Plate 31.

*Calyx.*—Shape—funnel. Size—small. Aspect—smooth. Odor when rubbed—none. Color—Light Cress Green, Plate 31.

*Peduncle.*—Length—short. Aspect—rough. Color—Cress Green, Plate 31. Strength—bending; slender.

*Opening.*—Bud opens up well. Is not affected by adverse weather conditions.

Bloom:
*Size.*—Small. Average size when fully expanded, 2 inches.
*Borne.*—In rounded clusters.
*Stems.*—Short; normal.
*Form.*—When first open—cupped. Permanence—flattens.
*Petalage.*—Semi-double (full but open center). Number of petals under normal conditions, 25–30.
*Color.*—Center of flower—Spectrum Red, Plate 1, overcast with Rose Doree, Plate 1. Outer petals—Rose Doree, Plate 1. Base of petals—Pale Pinkish Buff, Plate 29. Inside of petals—Spectrum Red, Plate 1, lightly overcast with Rose Doree, Plate 1, and with White, Plate 53, extending up about one-fourth of the petal from the base, thus giving the appearance of a white, Plate 53, eye. Reverse of petals—Spectrum Red, Plate 1, lightly overcast with Begonia Rose, Plate 1, and with White, Plate 53, extending up about one-fourth of the petal from the base. General tonality from a distance—Spectrum Red, Plate 1, overcast with Rose Doree, Plate 1.
*Discoloration.*—General tonality at end of first day—Spectrum Red, Plate 1, overcast with Rose Doree, Plate 1. Second day—Spectrum Red, Plate 1, overcast with Begonia Rose, Plate 1. Third day—Rose Doree, Plate 1.

Petals:

*Texture.*—Thin. Are not affected by wet or hot weather.

*Appearance.* — Inside — satiny. Outside—shiny.

*Form.*—Oval; notched.

*Arrangement.*—Imbricated (regularly arranged shinglelike). Petaloids in center—few and small.

*Persistence.*—Drop off cleanly.

*Fragrance.*—None.

*Lasting quality.*—On the plant—long, retaining a clear color for four or five weeks.

Genital organs:

*Stamens, anthers.* — Small, few. Color—Capucine Yellow, Plate 3. Arrangement—regular around styles.

*Stamens, filaments (threads).*—Short. Color—Sulphur Yellow, Plate 5.

*Pollen.*—Color—Pale Yellow-Orange, Plate 3.

*Styles.*—Bunched, of uneven length. Short, thin.

*Stigmas.*—Color—Light Orange-Yellow, Plate 3.

*Ovaries.*—All enclosed in calyx.

*Plant*

Form: Bush.

Growth: Vigorous and compact.

Foliage: 5 to 7 leaflets.

*Size.*—Medium.

*Quantity.*—Normal.

*Color.*—New foliage—upper side—Oil Green, Plate 5; under side—Lettuce Green, Plate 5. Old foliage—upper side—Dark Cress Green, Plate 31; under side—Light Cress Green, Plate 31.

*Shape.*—Oval pointed.

*Texture.*—Upper side—glossy; under side—smooth. Ribs and veins—ordinary.

*Edge.*—Serrated (saw toothed).

*Serration.*—Single, small.

*Leaf stem.*—Color—Light Cress Green, Plate 31. Under side—hooked prickles.

*Stipules.*—Short, bearded.

*Disease resistance.*—Resistant.

Wood:

*New wood.*—Color—Absinthe Green, Plate 31. Bark—smooth.

*Old wood.*—Color—Olive Green, Plate 4. Bark—smooth.

Thorns:

*Quantity.*—On main stalks from base and on laterals from stalk—none.

*Prickles.*—On main stalks—none. On laterals—few. Color—Lettuce Green, Plate 5.

*Short needles.*—Quantity—on main stalks and on laterals—none.

I claim:

A new and distinct variety of rose plant of the polyantha class, characterized as to novelty by its similarity in general habits to its parent "Triumph d'Orleans" (unpatented), except for its larger and brighter individual florets in the clusters, by the Spectrum Red, lightly overcast with Rose Doree color and White eye of the blooms, by the absence of thorns on the plant except for sharp hooks on the mid-rib of the under surface of the leaves, and by its freedom and ease of bloom when used as a pot plant, substantially as shown and described.

EUGENE S. BOERNER.

No references cited.